United States Patent [19]
Gross et al.

[11] Patent Number: 6,078,842
[45] Date of Patent: Jun. 20, 2000

[54] ELECTRODE AND IONTOPHORETIC DEVICE AND METHOD

[75] Inventors: Joseph Gross, Dublin, Ireland; Zvi Nitzan, Petah-Tikva, Israel; Izrail Tsals, Sudbury, Mass.

[73] Assignee: Elan Corporation, plc, Dublin, Ireland

[21] Appl. No.: 08/997,404

[22] Filed: Dec. 23, 1997

Related U.S. Application Data

[60] Provisional application No. 60/054,647, Apr. 8, 1997.

[51] Int. Cl.$^7$ ......................................................... A61N 1/04
[52] U.S. Cl. ............................................................ 607/152
[58] Field of Search ..................................... 607/115, 139, 607/140, 152

[56] References Cited

U.S. PATENT DOCUMENTS

| | | |
|---|---|---|
| 1,033,867 | 7/1912 | Blenkner et al. . |
| 1,786,341 | 12/1930 | Last .......................................... 604/140 |
| 1,899,770 | 2/1933 | Oppenheimer . |
| 2,110,618 | 3/1938 | Dee St Cyr . |
| 2,469,771 | 5/1949 | Jeppson . |
| 2,716,981 | 9/1955 | More . |
| 3,279,468 | 10/1966 | Le Vine . |
| 3,298,368 | 1/1967 | Charos . |
| 3,447,537 | 6/1969 | King ........................................ 607/140 |
| 3,477,537 | 11/1969 | King . |
| 3,971,387 | 7/1976 | Mantell . |
| 4,211,222 | 7/1980 | Tapper . |
| 4,248,247 | 2/1981 | Ware et al. . |
| 4,317,457 | 3/1982 | Guillot . |
| 4,365,634 | 12/1982 | Bare et al. . |
| 4,522,211 | 6/1985 | Bare et al. . |
| 4,580,339 | 4/1986 | Ioffe . |
| 4,655,232 | 4/1987 | Ficke . |
| 4,725,263 | 2/1988 | McNichols et al. . |
| 4,736,752 | 4/1988 | Munck et al. . |
| 4,763,660 | 8/1988 | Kroll et al. . |
| 4,867,166 | 9/1989 | Axelgaard et al. ....................... 607/152 |
| 5,038,796 | 8/1991 | Axelgaard et al. . |
| 5,067,478 | 11/1991 | Berlant . |
| 5,070,862 | 12/1991 | Berlant . |
| 5,085,227 | 2/1992 | Ramon . |
| 5,160,316 | 11/1992 | Henley . |
| 5,169,384 | 12/1992 | Bosniak et al. . |
| 5,246,418 | 9/1993 | Haynes et al. . |
| 5,310,103 | 5/1994 | Haynes . |
| 5,352,315 | 10/1994 | Carrier et al. . |
| 5,356,632 | 10/1994 | Gross et al. . |
| 5,405,317 | 4/1995 | Myers et al. . |
| 5,431,625 | 7/1995 | Fabian et al. . |
| 5,433,441 | 7/1995 | De Clavier . |
| 5,496,363 | 3/1996 | Burgio et al. . |
| 5,498,235 | 3/1996 | Flower . |
| 5,499,967 | 3/1996 | Teillaud et al. . |
| 5,523,090 | 6/1996 | Znaiden et al. . |
| 5,527,357 | 6/1996 | Springer, Jr. . |
| 5,792,097 | 11/1998 | Reddy ....................................... 604/20 |

FOREIGN PATENT DOCUMENTS

| | | | |
|---|---|---|---|
| 0 225 556 | 6/1987 | European Pat. Off. ....... | A61M 37/00 |
| 0 293 893 | 12/1988 | European Pat. Off. ......... | A61N 1/30 |
| 0 470 338 | 2/1992 | European Pat. Off. ......... | A61N 1/30 |
| 2177 928 | 2/1987 | United Kingdom ............ | A61N 1/30 |
| WO 92/04937 | 4/1992 | WIPO ............................. | A61N 1/30 |
| WO 94/17853 | 8/1994 | WIPO ............................. | A61N 1/30 |

*Primary Examiner*—William E. Kamm
*Attorney, Agent, or Firm*—Kathleen L. Maher

[57] ABSTRACT

An improved electrode and iontophoretic device and method where the electrode exhibits varied resistance. The electrode is made of a conductive material and applied to a flexible substrate. The variation in resistance can be achieved by varying the thickness of the electrode across its length or by varying the conductivity of the material across the area of the electrode or a combination of both. A pair of such electrodes may be used with a power source in electrical relation thereto and applied over a layer of agent to the skin to deliver the agent into the skin iontophoretically. The pair of electrodes may be shaped so as to cover a portion of the face, hands, feet or other body parts to iontophoretically apply particular agents to those areas.

30 Claims, 6 Drawing Sheets

ELECTRODE AND IONTOPHORETIC DEVICE AND METHOD

RELATED APPLICATION

This application is based on U.S. Provisional Application No. 60/054,647 filed Aug. 4, 1997 and now abandoned.

TECHNICAL FIELD

The present invention relates to an improved electrode and, more particularly, to an electrode for use in an iontophoretic device and method for the transcutaneous, delivery of chemicals, such as various drugs, nutritional agents and cosmetics into the skin.

BACKGROUND OF THE INVENTION

The transcutaneous transfer of a chemical, i.e., the transfer of a chemical into the skin of a patient, is widely used in drug delivery applications. A number of transcutaneous delivery systems are known. Perhaps the simplest involves placing the chemical to be delivered in contact with the patient's skin and allowing the chemical to penetrate the skin by osmosis and related spontaneously occurring mass transport phenomena. This technique is the most common one for applying various cosmetic lotions, such as skin softeners and the like, to the skin. The lotion is simply spread on the skin and is allowed to remain there, enabling some components of the lotion to penetrate the skin.

A more sophisticated transcutaneous chemical delivery technique, known as iontophoresis, uses electrical energy to induce the chemical to penetrate the skin. Iontophoresis allows better control of the rate of delivery of the chemical and of the depth of penetration of the chemical into the skin. Furthermore, iontophoresis enables larger molecules to penetrate the skin.

Stripped to its bare essentials, iontophoresis involves the application of an electromotive force to drive ionic chemicals into the skin. An iontophoretic device includes two electrodes. At any one time, one of the electrodes has in its vicinity the ionic species to be driven into the skin. The other electrode serves to close the electrical circuit through the skin. In use, both electrodes are brought into contact with the skin. An electromotive force is applied to the electrodes, creating an electrical circuit between the two electrodes which runs through the skin and which drives the ionic chemical species away from the first electrode and into the skin.

Biomedical electrodes for sensing biomedical signals such as those used in measuring electrocardiographic (EKG) or electroencephalagraphic signals are known. Moreover, electrodes for passive sensing of transcutaneous electrical currents, or for introducing electrical energy transcutaneously, are known.

None, however, are optimal for providing an even current distribution across the electrode. In certain applications, it is desirable to have even current distribution or potential across the electrode. This is accomplished by providing an electrode that exhibits high conductivity and low resistance. At present, there are no electrode that exhibit these qualities.

In addition, none of the existing electrodes are optimal for use in areas of the body where skin depth changes and sensitivity to electrical current vary across any given area of the body. Such an electrode or device should have even current distribution as well as low resistance in certain areas to avoid harming the more sensitive areas of the skin surface through burning or electrolysis. Moreover, none of the existing electrode technology is optimal for use in contoured areas of the body where there are high concentration of nerve endings, such as the face, hands, feet, or head. In such cases where there are high concentrations of nerve endings there is an increased possibility from the existing devices for sensitivity to iontophoresis.

There are also particular medicaments that may be most effectively delivered transcutaneously. For example, some acne medications are most effective when they are delivered directly into the skin's surface in the area in which the acne appears. These situations are ripe for iontophoretic delivery of such a medicament. Presently there are no electrodes, iontophoretic devices or methods that effectively deliver such agents through the skin without possibly harming the skin. There are no existing electrodes, or iontophoretic devices or methods that take into account the variations in skin sensitivity to the introduction of electric current from one area of the skin to another.

There are also situations where transcutaneous application of a particular medicament may be messy, or may require isolation of the area during treatment of that area. For example, nail fungal treatments must be applied directly to the toe or finger nail. During such treatments, the patient may want to isolate such medicament while the treatment is in progress. In such cases, it is preferable that the electrodes or iontophoretic device be completely disposable, as well as capable of conformation to the applicable contours of the body. In addition, the electrodes and device should be capable of isolating such an area during treatment to decrease the spread of any medicament or condition to other areas, clothing or the like. To be completely disposable and conformable, such a device must be flexible, relatively thin and be made of inexpensive materials. At present, there are several patents directed to disposable electrodes. However, none of the prior art disclosed a disposable electrode for use in iontophoresis where the electrode has varied resistivity to provide for a predetermined level of current distribution and to compensate for variations in the sensitivity of certain skin areas and thus avoid harmful burning.

Thus, there is a widely recognized need for, and it would be highly advantageous to have, an electrode that is optimized both compositionally and structurally to minimize or eliminate irritation to the user's skin.

There is a further need for an iontophoretic device and method that utilize electrodes that are optimized both compositionally and structurally to minimize or eliminate irritation to the user's skin.

There is another need for an electrode that varies the resistance across the area of the electrode to compensate for variations in skin sensitivity.

There is yet a further need for an iontophoretic device and method that incorporates at least one electrode that varies the resistivity across the area of the electrode to compensate for variations in skin sensitivity.

There is still a further need for an electrode that is flexible and disposable, and that is varied in thickness across the area of the electrode so as to vary the resistivity and avoid harmful burning to sensitive skin areas.

There is yet another need for a method of introducing an agent into the skin where the electrode receiving the current has a varied resistance so that the agent may effectively pass into the skin yet avoid burning or otherwise harming the skin.

There is still a further need for a device and method that effectively eliminates cellulite below the skin surface by introducing current to the skin via an electrode where the electrode has a varied thickness across the area of the electrode.

SUMMARY OF THE INVENTION

As will be seen, the present invention overcomes these and other disadvantages associated with prior art electrodes, and iontophoretic devices and methods.

According to the present invention there is provided an improved electrode where the electrode has a flexible, nonconductive substrate, and a layer of electrically conductive material applied to a portion of the surface of the nonconductive substrate. The conductive material has varied electrical resistance.

There is also provided an improved device for the iontophoretic delivery of an agent to the skin surface including a flexible, substrate, a pair of spaced apart electrodes. The electrodes are made of electrically conductive material applied to a portion of the surface of the substrate. At least one of the electrodes has varied electrical resistance. The device also includes a power supply in electrical communication with each electrode. When the power supply is in electrical communication with the electrodes, current passes to the skin causing an agent applied to the surface of the skin to be delivered below the skin surface.

There is still further provided an improved method for delivering an agent into the skin. The method includes fixing a pair of electrodes to a portion of surface area of a flexible substrate. The electrodes are spaced apart and at least one of the electrodes has varied electrical resistance. The method further includes the steps of applying an agent to the skin surface, causing the electrodes to contact the skin surface, and introducing electrical current from a power source to the electrodes.

The electrode, iontophoretic device and method of the present invention are improvements over the prior art in that the electrode, device and method prevent skin irritation in normal use by varying the resistance of at least one electrode. The resistance is varied by one or a combination of the following ways: (1) by varying the thickness of the conductive material; (2) by varying the conductivity of the material used to comprise the electrode; or (3) by varying the geometry of the conductive material. As a result of the variation in resistance, the improved electrode exhibits varied vertical and/or lateral variation in electrical resistivity. Vertical resistivity or resistance is the resistance across the thickness of a particular point on the electrode and the lateral resistivity or resistance is the resistance measured across the particular length of the electrode. Vertical variation of the electrical resistivity of the conductive ink coating is particularly important in preventing "hot spots", the focusing of electric current at abnormally conductive areas of the user's skin, such as small open wounds. These hot spots are prevented by making the conductive ink coating significantly more sensitive to electrical current, on the side of the conductive ink coating that comes into direct contact with the user's skin, than elsewhere. Varied resistance across the electrode also maintains the electrical current density controlled over the entire surface of the electrode.

The scope of the present invention also includes the application of the device of the present invention to iontophoresis for cosmetic purposes, and the application of iontophoresis to the reduction of subcutaneous cellulite deposits. A variety of topical creams and lotions are available for reducing cellulite, but a safe and effective method of the iontophoretic application of those creams and lotions has not been disclosed heretofore.

Thus, it is an object of the present invention to provide an improved electrode, iontophoretic device and method having varied resistance so as to achieve uniform distribution of current.

It is a further object of the present invention to provide an improved electrode, iontophoretic device and method having varied resistance so as to reduce any harm to the skin.

It is a further object of the present invention to provide an electrode that varies the resistance across the area of the electrode to compensate for variations in skin sensitivity.

It is still a further object of the present invention to provide an electrode that is flexible and disposable, and exhibits varied resistance to avoid harm to the skin.

It is yet a further object of the present invention to provide a method of introducing an agent into the skin where the electrode receiving the current has a varied resistance so that the agent may effectively pass into the skin yet avoid burning or otherwise harming the skin.

It is still a further object of the present invention to provide a device and method that effectively eliminates cellulite below the skin surface by introducing current to an electrode where the electrode has a varied thickness across the area of the electrode.

Other objects, features and advantages of the present invention will be apparent upon reading the following specification taken in conjunction with the drawings and appended claims.

DESCRIPTION OF THE PREFERRED EMBODIMENTS

Figure 1:
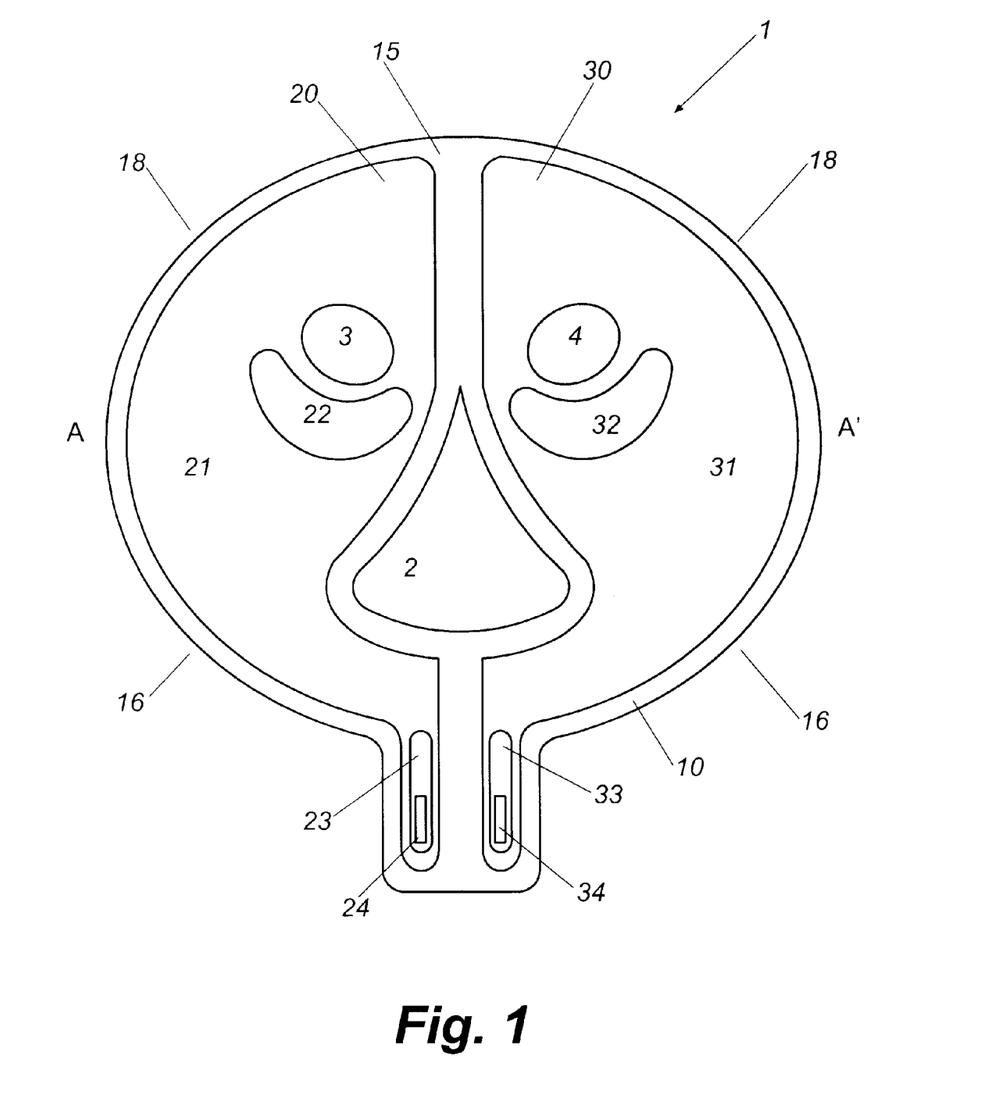
FIG. 1 is a front view of a preferred embodiment of the present invention.

Referring now to the drawings, in which like numerals indicated like elements throughout the several views, FIG. 1 discloses a front view of a first embodiment of the present invention in the form of a first face mask 1. The first face mask 1 is made up of an insulating base 10 on which are printed a left electrode 20 and a right electrode 30, separated by an insulating gap 15. Insulating base 10 is provided with a nose hole 2, a left eye hole 3, and a right eye hole 4, so that the user's nose and eyes are not subjected to iontophoresis. The insulating base 10 is preferably made of tissue paper 11. The tissue paper 11 should be made of a hygienic, non-woven, non-flammable, water repellent material. One such paper is a 60 grade tissue paper made by Walkisoft.

Left electrode 20 consists of a lower layer 21 and an upper layer, printed on top of lower layer 21 and entirely within the area of lower layer 21. The upper layer is made of two disjoint parts, a cheek part 22 and a chin part 23. Similarly, right electrode 30 consists of a lower layer 31 and an upper layer in two parts, a cheek part 32 and a chin part 33. On the lower halves of chin parts 23 and 33 are placed two conductive adhesive patches 24 and 34. Adhesive patches 24 and 34 serve as attachment points for the leads (not shown) that provide electrical current, and also serve to hold packaging material for the first face mask 1 in place.

First face mask 1 also preferably includes a plurality of perforated lines 16 or impressed lines 18 to facilitate folding portions of the mask so as to effect a better fit on the user's face. The embodiment of the first face mask 1 shown in FIG. 1 has perforated lines 16 on either side of the chin area, and impressed lines 18 in the two temple areas.

Figure 2:
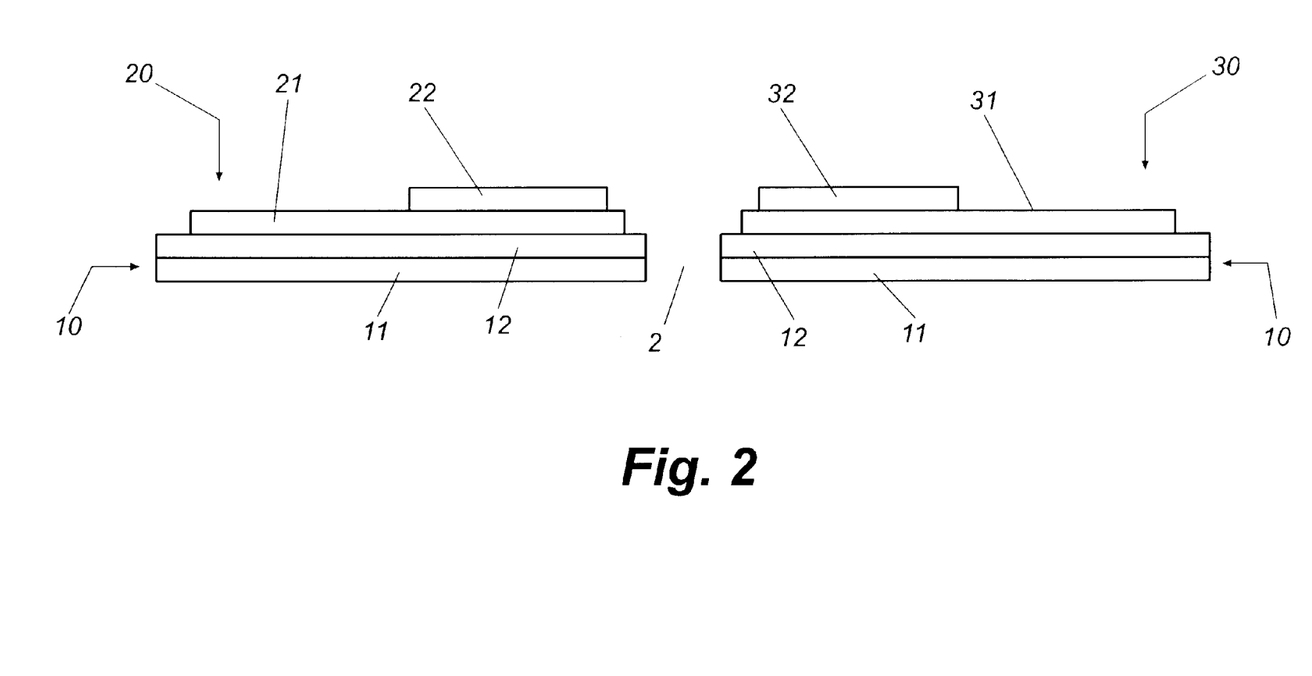
FIG. 2 is a cross sectional view of the preferred embodiment of FIG. 1.

FIG. 2 provides a cross-section view of the first face mask 1. A layer of lacquer 40 is printed onto the top surface of the base 10. The lacquer is preferably a food-grade lacquer. The lower layers 21 and 31 are printed onto the lacquer and are preferably made of an electrically conductive ink. The lower layers are preferably of uniform thickness so as to evenly distribute the current throughout the electrode. The upper layers are printed onto the lower layers 21 and 31. The upper layers are preferably made of an electrically conductive ink, and has a higher resistance than the outer layer. Other means of fixing the lower or upper layers or the lacquer 40 to the base 10 include laser printing, rotor gravure, stenciling and other methods known in the art.

The vertical and/or lateral resistivity of the lower layers 21, 31 and the upper layers may be varied by varying several factors. These include the thickness of the lower or upper layers and/or the conductivity of the materials used to make up the lower and upper layers. The conductivity may be altered by varying the material used or by adding or adjusting carbon powder concentration. The preferred combination ranges from 6.5% and 12.5% by weight of medical grade carbon powder to the ink before applying the ink to the outer layer. Suitable carbon powder includes "Super P", manufactured by M.M.M. Carbon of Willebrock, Belgium. The preferred ink is type "GO3-95" manufactured by Sicpa Swiss.

As mentioned above, variations of vertical and/or lateral electrical resistivity may be achieved by a number of ways including varying the thickness of the layers, and/or varying the composition of the layers so as to affect conductivity. In addition, variations to resistivity may also be achieved in the present invention by superposing several layers of uniform thickness and uniform composition but of different areas. In this way, the overall thickness of the electrode varies and results in a variation of the lateral and vertical resistivity across the electrode.

It is preferable that the carbon power of the lower layers 21 and 31 be adjusted to make the electrical resistance, measured between two probes placed one centimeter apart on lower layer 21 or on lower layer 31, between about 100 ohms and about 1000 ohms. This measurement is referred to as lateral resistance. It is also preferable that the lateral resistance of cheek parts 22 and 32, and chin parts 23 and 33, have similar ranges.

In FIG. 2, insulating base 10 is shown as being made up of two layers, the tissue paper layer 11 and the lacquer layer 40. The lacquer layer 12 is applied to tissue paper layer 11 before printing electrodes 20 and 30, in order to prevent the conducting ink from seeping through the tissue paper layer 11. FIG. 2 also shows that electrodes 20 and 30 are two-layer structures: the portion of left electrode 20 shown includes lower layer 21 and cheek part 22 of the upper layer, and the portion of right electrode 30 shown includes lower layer 31 and cheek part 32 of the upper layer.

Electrodes 20 and 30 are fabricated with variable thickness in order to provide them with laterally varying resistance to electrical current, thereby controlling the density of the electrical current flowing therein. Electrodes 20 and 30 are thicker where current density must be reduced: near the points of attachment of the electrodes, at adhesive patches 24 and 34, where the lines of current flow converge, and above the user's cheeks, where the skin is especially sensitive, so as to prevent harm to the skin.

Figure 3A:
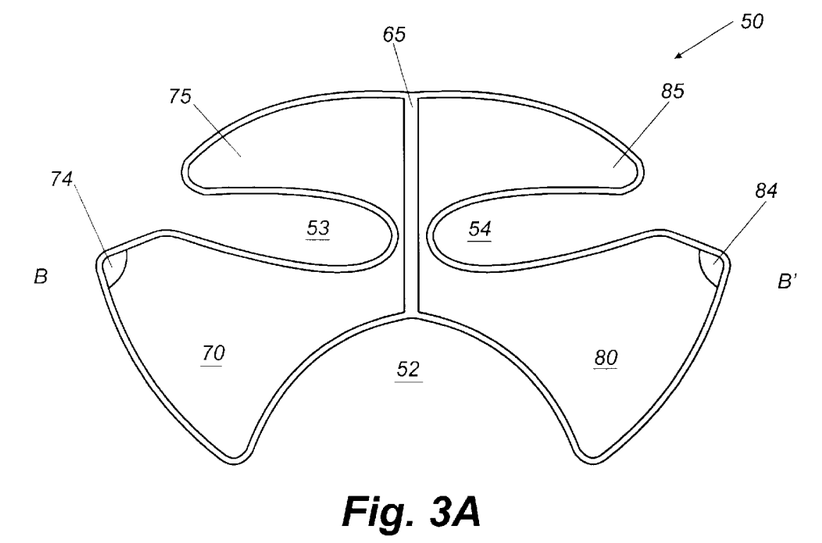
FIG. 3A is a front view of a second embodiment of the present invention.
Figure 3B:
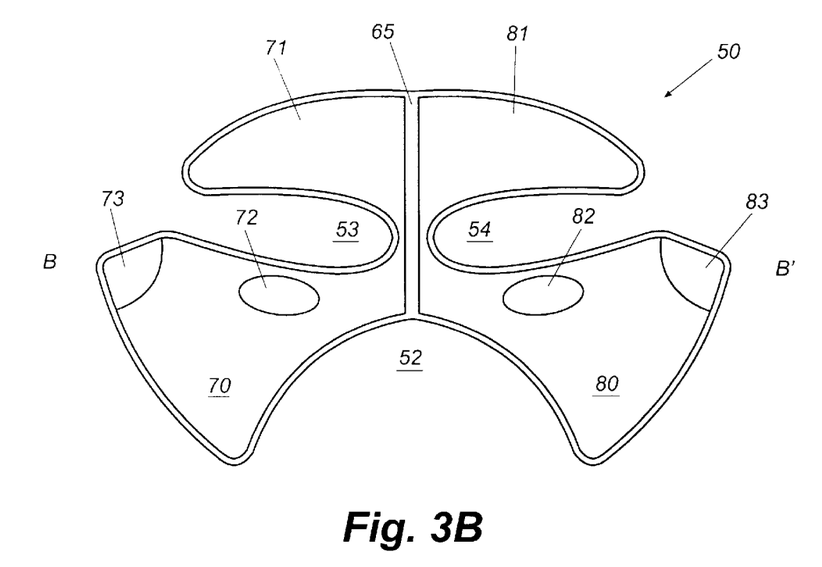
FIG. 3B shows the embodiment of FIG. 3A with the topmost ink layer removed.
Figure 4:
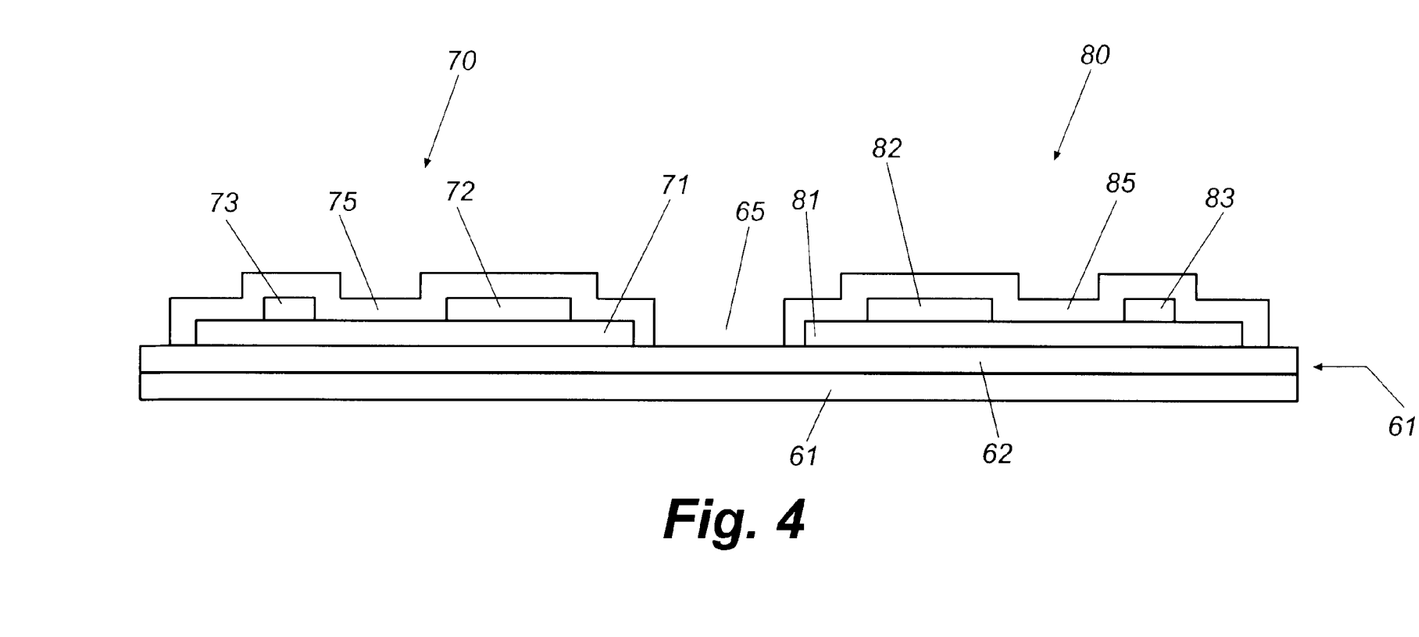
FIG. 4 is a cross sectional view of the embodiment of FIG. 3A.

FIGS. 3A, 3B and 4 show a second embodiment of the present invention in the form of a second face mask 50. Like the first face mask 1, the second face mask 50 is made up of an insulating base 60 on which are printed a left electrode 70 and a right electrode 80, separated by an insulating gap 65. Face mask 50 is shaped with a mouth opening 52 and eye openings 53 and 54, and therefore does not need perforated lines.

Electrodes 70 and 80 of the second face mask 50 are multilayer structures. Only an upper layer 75 of electrode 70 and an upper layer 85 of electrode 80 are shown in FIG. 3A. FIG. 3B shows second face mask 50 with upper layers 75 and 85 removed, showing the remaining layers of electrodes 70 and 80: lower layers 71 and 81, and disjoint middle layers that include cheek parts 72 and 82, and temple parts 73 and 83. The characteristics of lower layers 71 and 81, and cheek and temple parts 72, 73, 82 and 83 of the middle layers, are adjusted to make the electrical resistance, measured between two probes place one centimeter apart on any one of these layers in isolation, between about 100 ohms and about 1000 ohms. The characteristics of upper layers 75 and 85 are adjusted to make the electrical resistance per unit area, measured perpendicularly to either upper layer 75 or upper layer 85 in isolation, between about 500 ohms per square centimeter and about 5000 ohms per square centimeter. As stated above, the vertical and/or lateral resistivity may be adjusted by adjusting the thickness of any of the layers, or by adjusting the composition of the material in any of the layers. The composition may be adjusted by altering the amount of carbon in the conductive ink. Moreover, any combination, or permutation of these options may be used.

Two conductive adhesive pads 74 and 84 are located above the temple ends of electrodes 70 and 80. Like adhesive pads 24 and 34, adhesive 74 and 84 serve as attachment points for the leads that provide electrical current, and also serve to hold packaging material for second face mask 50 in place. When the second face mask 50 is in place, adhesive patches 74 and 84 lies close to the user's ears, so that the leads can be draped over and behinds the user's ears.

FIG. 4 is a cross sectional view of second face mask 50, across cut B-B'. Like insulating base 10, insulating base 60 is made of a tissue paper layer 61 and a lacquer layer 62. Upper layers 75 and 85 are shown totally covering middle layer parts 72, 73, 82 and 83, and lower layers 71 and 81.

In first face mask 1, a laterally varying resistance is obtained in electrodes 20 and 30 by printing electrodes 20 and 30 in layers. Similarly, in second face mask 50, a resistance that varies both laterally and vertically may be obtained by printing electrodes 60 and 70 in layers so that the overall thickness of the electrodes 60, 70 are not uniform throughout. Alternatively, varying resistance may be obtained in a single-layer electrode of uniform thickness by varying the conductivity characteristics, such as the electrical conductivity of the material, and/or the weight percentage of carbon powder in the conductive ink, laterally across the layer.

Figure 5A:
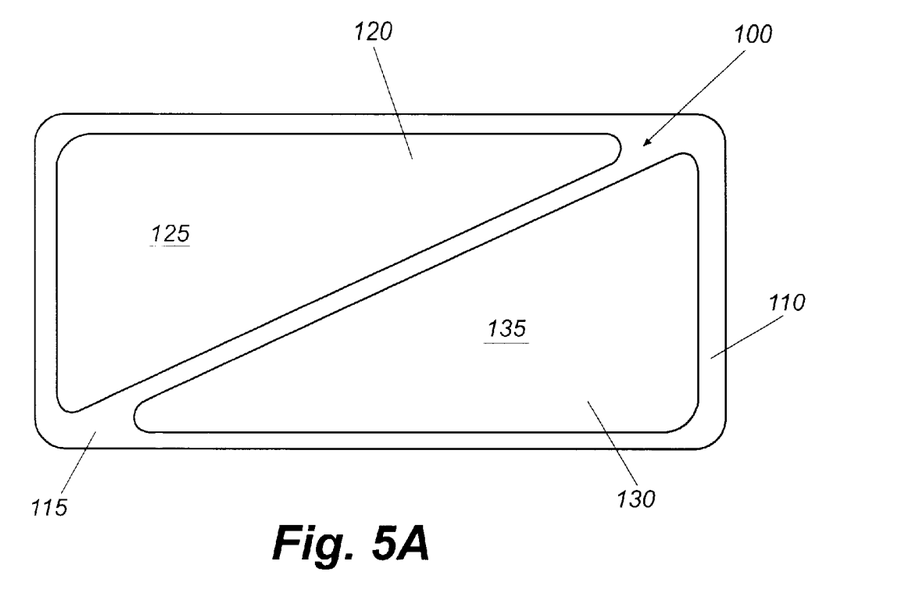
FIG. 5A shows a front view of a third embodiment present invention in the form of a pad suitable for reducing subcutaneous cellulite.
Figure 5B:
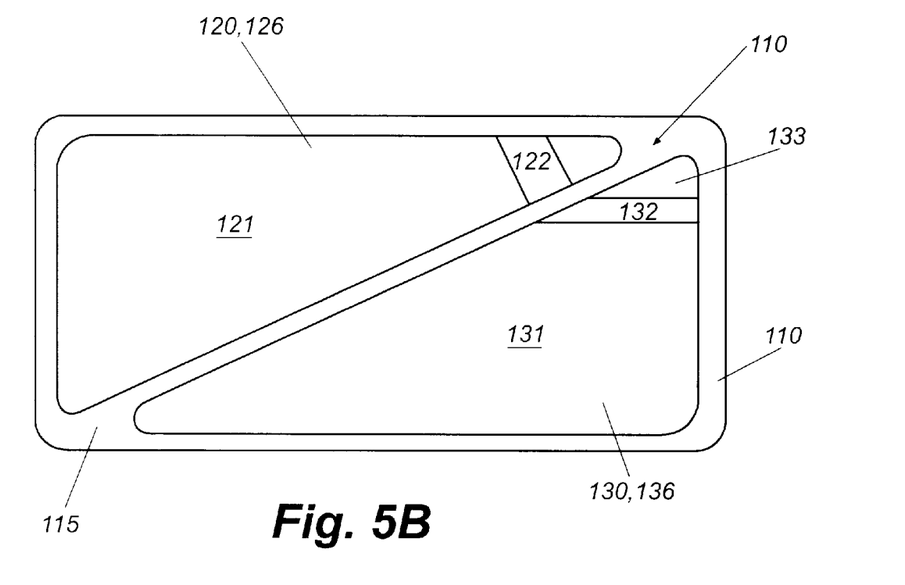
FIG. 5B shows embodiment of FIG. 5A with the topmost ink layer removed.

FIGS. 5A and 5B show a skin pad 100 of the present invention configured for the reduction of subcutaneous cellulite deposits. Like first and second face masks 1 and 50, skin pad 100 consists of an insulating base 110 on which are printed two electrodes, 120 and 130. In this case, however, electrodes 120 and 130 are two-layer structures of uniform thickness. In FIG. 5A, only upper layers 125 and 135 are visible. Like upper layers 75 and 85 of face mask 50, upper layers 125 and 135 of skin pad 100 are characterized by a resistance per unit area, measured perpendicularly to either layer in isolation, of between about 500 ohms per square centimeter and about 5000 ohms per square centimeter. In FIG. 5B, upper layers 125 and 135 have been removed, exposing lower layers 126 and 136 that are printed in three sections, each of a different electrical resistance, as measured between two probes about one centimeter apart. Although the characteristic resistance of each section is between 100 ohms and 1000 ohms, section 122 of layer 126 and section 132 of layer 136 each preferably have a characteristic resistance of about half the characteristic resistance of section 121 of layer 126 and section 131 of layer 1346. In this case, the varying resistivity of electrodes 120 and 130 is obtained by printing the sections of layers 126 and 136 with different weight percentages of the carbon powder.

In use, electrical leads (not shown), are clipped to the reduced resistance parts 123, 133 of electrodes 120 and 130. Alternatively, adhesive patches similar to adhesive patches 24 and 34 may be provided on upper layers 125 and 135. As in the case of insulating base 10, insulating base 110 preferably consists of a tissue paper layer 111 and a lacquer layer 112, with electrodes 120 and 130 being printed on the lacquer layer 112.

As an alternate design in any of the embodiments discussed above, the lower, less resistive layers may be printed or otherwise applied to the base of the device in a grid shape having recesses therein in an effort to reduce the amount of material used and ultimately reduce cost. The grid may be a plurality of squares, rectangles, honeycomb-design or other shapes.

For cosmetic, nutritional or medicinal application to the face, a suitable agent is placed on the skin surface of the user's face and electrical current is applied to the agent, using the either the first or second face masks 1, 50 of the present invention, to drive the agent into the skin. Because the physical form of the agent typically is a lotion, a cream or a gel, the mixture is referred to herein generally as "agent"; but the scope of the present invention includes all such mixtures. Preferably, a lotion used for cosmetic purposes of the user's face includes vitamin A and/or vitamin E, or alpha hydroxy acid; and a medicinal agent may include tetracycline, other antibiotics, anti-acne medicaments or anti-toxins.

To reduce cellulite deposits, a user would apply lotion used to reduce cellulite deposits and then place either the first or second face masks 1, 50, or the skin pad 100 of the present invention over the face to drive the cellulite reducing agent into the skin. Such agents include caffeine extract, theophylline extract, ginkgo extract, silisium, magnesium, and/or gola.

Applicant also anticipates that this invention may be altered in shape to conform to other particular body parts. For example, the present invention includes at least one electrode in the shape of a hand or finger for use in treating skin disorders of the hand, fingers, or fingernails, such as chronic skin dryness and nail fungal disease. Such an electrode would have the characteristics of the electrodes described above. Agents applied to the skin to treat such disorders include but are not limited to vitamin A, vitamin E, anti-fungal agents and alpha hydroxy acid. Moreover, it is further anticipated that the present invention would also include devices and methods for treating skin disorders of the feet, toes and toe nails. These include but are not limited to athlete's foot medicament, anti-fungal agents and skin moisturizers. Such a device would include at least one electrode in the shape of a human foot or toe. The electrode would have the characteristics described herein. The user would apply a particular agent suited for treating the skin disorder of the foot, toe or toenail and apply the device over the affected area and apply power to drive the agent into the skin.

Applicant further anticipates similar application of the present invention to treat scalp disorders such as psoriasis, and baldness. Agents used in the treatment of head and scalp disorders include: minoxidil, anti-dandruff agent and anti-psoriasis medicament. It is also anticipated that the present invention be applied to the skin surface of the penis to treat male impotency. Agents used in the treatment of male impotency include penile erection stimulants such as prostaglandin. The examples of use of this invention to treat certain disorders are by way of example and are not meant to limit the scope of the present invention. It is anticipated that the present invention have numerous applications to a variety of body parts to treat a number of different ailments.

Figure 6:
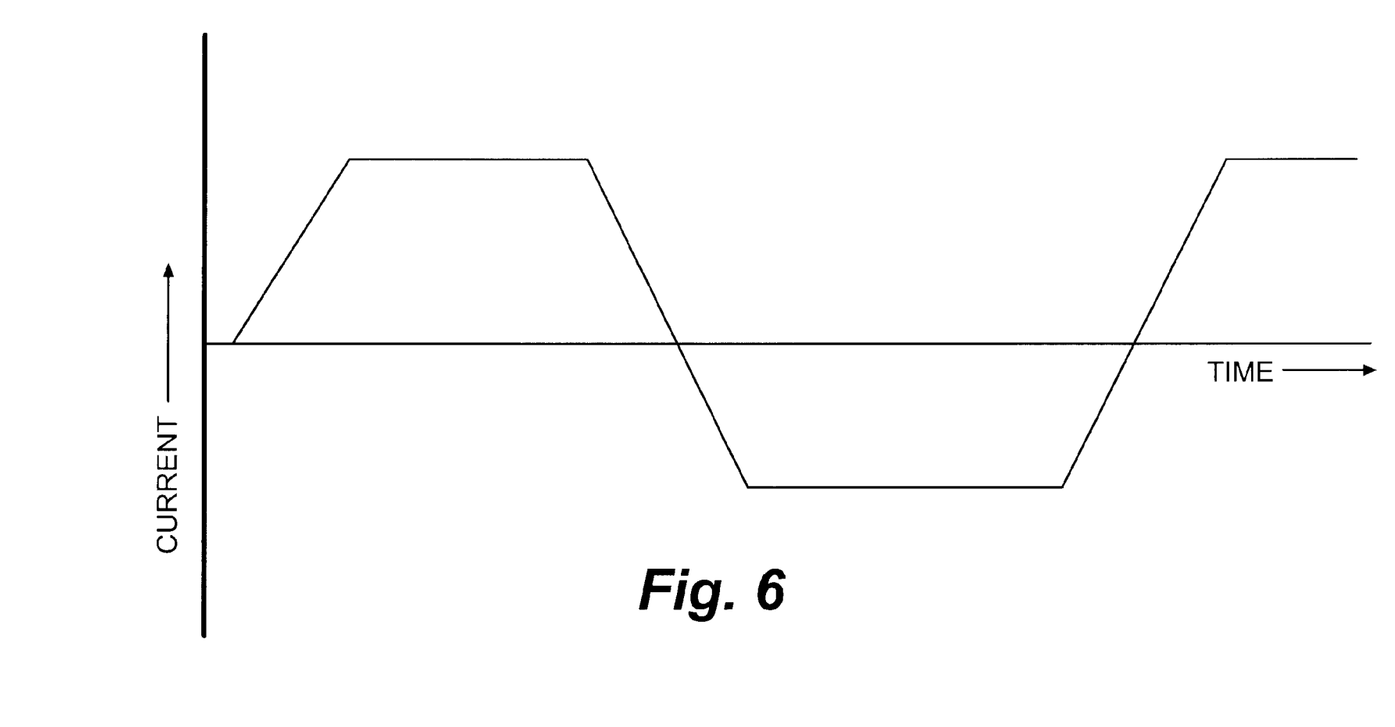
FIG. 6 shows a preferred current waveform for the application of electric current to the electrodes of the skin pad of the present invention.

Preferably, the electrical current used in the present invention is direct current, applied in sessions of alternating polarity. In this way, the chemicals of the lotion are driven in one direction by the electrical current of the entire duration of a session, and in the opposite direction for the entire direction of the subsequent session. In addition, alternating the polarity of the sessions prevents undesirable electrolysis within the skin tissue. FIG. 6 shows a preferred current waveform. Note that the electrical current is ramped on, i.e., increases gradually from zero to a maximum value, and then ramped off, i.e., decreases gradually back to zero, to prevent irritation associated with a sudden onset of current. The preferred electrical current density is between about 50 microamperes per square centimeter and about 500 microamperes per square centimeter, to effectively reduce the cellulite without irritating or burning the skin. The preferred pulse duration is between about 30 seconds and about 120 seconds for each period of full current, with ramp duration, from zero current to full current or from full current to zero current, of about one second.

While the invention has been described with respect to a limited number of embodiments, it will be appreciated that many variations, modifications and other application of the invention may be made. For example, the substrate may be made of a thin flexible inexpensive material other than tissue paper, such as cloth or polyester sheet. It is also anticipated that at least one electrode having varied resistance may be made of a molded elastomer. The electrode would be molded in the shape of a human extremity such as a finger, or toe so as to be slipped onto the finger, toe or the like for treatment of skin or nail disorders or the like. Moreover, the lower layers may be made of other conductive materials such as metallic sheet or foil. In addition, it is anticipated that the lacquer and conductive materials may be applied to the base 10 by means other than silk screening, such as rotor gravure printing, laser printing, stenciling, lamination, extrusion and other means commonly known in the art.

Applicant also anticipates that the preferred embodiments described above may comprise a single electrode with a second electrode being attached to the user's body at a remote location. For example, it is anticipated that the face masks described above may comprise a single electrode and a second electrode may be held in the user's hand or otherwise located remotely from the face.

Applicant's invention has primarily focused on a pair of electrodes for use in iontophoretic applications. However, applicant anticipates that a complete iontophoretic device is encompassed in this invention. Such a device would include the pair of electrodes discussed in detail above, along with a power source electrically connected to the electrodes upon use. Such a power source would consist of a battery with sufficient power to provide the current and amperage required to effectively deliver the agent through the user's skin as set forth in detail above.

What is claimed is:

1. An improved electrode comprising:
   a flexible member; and
   electrically conductive material applied to at least a portion of the flexible member, the electrically conducive material having varied thickness.

2. The improved electrode of claim 1 wherein the flexible member is paper.

3. The improved electrode of claim 2 wherein the paper has a polymer backing in contact with the electrically conductive material.

4. The improved electrode of claim 1 wherein the electrically conductive material is a conductive ink.

5. The improved electrode of claim 1 wherein the electrically conductive material includes carbon powder.

6. The improved electrode of claim 5 wherein the carbon powder is characterized by a weight percentage of between about 6.5% and about 12%.

7. The improved electrode of claim 1 wherein the conductive material comprises a plurality of materials, at least one material having a different electrical conductivity from the other materials.

8. The improved electrode of claim 1 wherein the conductive material comprises a plurality of layers.

9. The improved electrode of claim 8 wherein the plurality of layers comprises a plurality of materials, where at least one material has a different electrical conductivity from the other materials.

10. The improved electrode of claim 8 wherein the surface area of at least one of the plurality of layers is different from the surface area of at least one other of the plurality of layers.

11. The improved electrode of claim 8 wherein the thickness of at least one of the plurality of layers is different from the thickness of at least one other of the plurality of layers.

12. The improved electrode of claim 8 wherein the resistance to electrical current of each layer of the plurality of layers is between about 100 ohms and about 1000 ohms when measured between two probes placed about one centimeter apart.

13. The improved electrode of claim 8 wherein the topmost layer of the plurality of layers is characterized by a resistance to electric current per unit area of between about 500 ohms per square centimeter and about 5000 ohms per square centimeter.

14. The improved electrode of claim 8 wherein the plurality of layers includes at least a lower layer and an upper layer, the lower layer being adjacent to the flexible member and the upper layer being adjacent to the lower layer.

15. The improved electrode of claim 14 wherein the lower layer has a lower resistance than the upper layer.

16. The improved electrode of claim 14 wherein the lower layer is grid shaped.

17. The improved electrode of claim 14 wherein the upper layer is non-conductive.

18. The improved electrode of claim 1 further comprising a means to secure the electrically conductive material to the surface of the skin of a mammal.

19. The improved electrode of claim 18 wherein the means comprises electrically conductive adhesive applied to a portion of the electrically conductive material.

20. The improved electrode of claim 1 wherein the flexible member is a molded to conform to the surface of a particular body extremity.

21. The improved electrode of claim 20 wherein the flexible member is molded by means of an injection molding process.

22. The improved electrode of claim 20 wherein the member is an elastomer having carbon powder suspended therein.

23. The improved electrode of claim 1 wherein the member is shaped to conform to the surface of a human finger.

24. The improved electrode of claim 1 wherein the member is shaped to conform to the surface of a human hand.

25. The improved electrode of claim 1, wherein the member is shaped like a glove.

26. The improved electrode of claim 1 wherein the member is shaped to conform to the surface of a human toe.

27. The improved electrode of claim 1 wherein the member is shaped to conform to the surface of a human foot.

28. The improved electrode of claim 1 wherein the member is shaped like a sock.

29. The improved electrode of claim 1 wherein the member is in the shape of a face mask having a forehead area, a temple area, a nose area, two cheek areas and a chin area.

30. The improved electrode of claim 29 wherein the face mask has a pair of holes anatomically corresponding to the eye areas in a human face.

* * * * *